United States Patent [19]

Valentine et al.

[11] 4,389,527

[45] Jun. 21, 1983

[54] PROCESS FOR THE PREPARATION OF DIHYDROCINNAMALDEHYDE DERIVATIVES

[75] Inventors: Roy H. Valentine, Caterham, Great Britain; Harold A. Brandman, Glen Ridge, N.J.

[73] Assignee: Givaudan Corporation, Clifton, N.J.

[21] Appl. No.: 278,968

[22] Filed: Jun. 30, 1981

[30] Foreign Application Priority Data

Jul. 4, 1980 [GB] United Kingdom ................ 8021949
Apr. 27, 1981 [GB] United Kingdom ................ 8112923
Jun. 16, 1981 [GB] United Kingdom ................ 8118538

[51] Int. Cl.$^3$ ............................................ C07C 45/46
[52] U.S. Cl. .................................. 549/438; 568/433; 568/435
[58] Field of Search ................ 568/433, 435; 549/438

[56] References Cited

U.S. PATENT DOCUMENTS 3,023,247  2/1962  Scriabine .
4,182,730  1/1980  Virgilio et al. .

FOREIGN PATENT DOCUMENTS 1057360  2/1967  United Kingdom ................ 568/433

OTHER PUBLICATIONS

Olah, Friedel–Crafts Reactions, vol. I, (1963), 202, 203, 327.
Scriabine, Bull. Soc. Chim. France, (1961), 1194–1198.
Berends et al., Perfumery & Essential Oil Record, vol. 58 (1967), 372–378.

Primary Examiner—Bernard Helfin
Attorney, Agent, or Firm—Robert F. Tavares

[57] ABSTRACT

This invention discloses a novel process for producing dihydrocinnamaldehyde derivatives which comprises reacting a benzene derivative with an alken-2-ylidene diacylate or an α-ethylenic aldehyde in trifluoroacetic acid (TFA).

16 Claims, No Drawings

PROCESS FOR THE PREPARATION OF DIHYDROCINNAMALDEHYDE DERIVATIVES

BACKGROUND OF THE INVENTION

A number of dihydrocinnamaldehyde (3-phenylpropionaldehyde) derivatives are important compounds in the fragrance industry, such as

- 3-[p-isopropylphenyl]-2-methyl-propionaldehyde also known as Cyclamen Aldehyde
- 3-[p-tert-butylphenyl]-2-methyl-propionaldehyde
- 3-[3,4-methylenedioxyphenyl]-2-methyl-propionaldehyde also known as Helional
- 3-[p-methoxyphenyl]-2-methyl-propionaldehyde
- 3-[p-tert-butylphenyl]-propionaldehyde
- 3-[p-n-butylphenyl]-2-methyl-propionaldehyde
- 3-[p-iso-butylphenyl]-2-methyl-propionaldehyde
- 3-[p-α-methylpropyl-phenyl]-2-methyl-propionaldehyde
- 3-[p-tert-butylphenyl]-3-methyl-propionaldehyde.

W. Berends and L. M. v.d. Linde discuss a number of dihydrocinnamaldehyde derivatives with regard to odor properties and method of synthesis in Perfumery and Essential Oil Record, 58, 372 (1967).

One of the methods described involved the reaction of a benzene nucleus with an α-ethylenic aldehyde or, preferably, with the corresponding alken-2-ylidene diacylates in the presence of titanium tetrachloride as catalyst. This method is described further in U.S. Pat. No. 3,023,247 wherein it is indicated that titanium tetrachloride is unique in its ability to direct the reaction in the desired manner.

SUMMARY OF THE INVENTION

This invention provides a novel process for preparing derivatives of 3-phenylpropionaldehyde by condensing an aromatic, i.e. benzene compound with an α-ethylenic aldehyde, presumably in the form of an alken-2-ylidene diacylate, by using trifluoroacetic acid. It is the surprising and unexpected finding of this invention that no additional catalyst such as titanium tetrachloride is required.

The process can suitably be run either by reacting the aromatic compound with the alken-2-ylidene diacylate in the presence of trifluoroacetic acid or the α-ethylenic aldehyde with a mixture of the aromatic compound, an acid anhydride or diketene and the trifluoroacetic acid.

Preferably, the process is run either by reacting the aromatic compound with an alken-2-ylidene diacylate in the presence of trifluoroacetic acid or by reacting an α-ethylenic aldehyde with a mixture of the aromatic compound, an acid anhydride or diketene and trifluoroacetic acid. The intermediate formed is hydrolyzed to the desired 3-phenylpropionaldehyde.

DESCRIPTION OF THE PREFERRED EMBODIMENTS

The critical finding of this invention is the use of trifluoroacetic acid to effect the reaction between an aromatic compound and an α-ethylenic aldehyde (or the corresponding alken-2ylidene diacylate) to provide the desired 3-aryl propionaldehyde derivative.

While the use of the trifluoroacetic acid to effect the desired reaction between an aromatic compound and an α-ethylenic aldehyde appears to be very general, it is preferred to apply the invention to the manufacture of odorants of the general formula

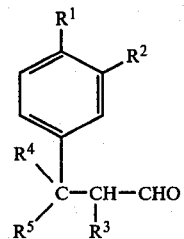

wherein:
- $R^1$ is isopropyl, n-butyl, sec. butyl, isobutyl, tert. butyl or methoxy when $R^2$ is hydrogen; or
- $R^1$ together with $R^2$ represents the methylene dioxy group; and
- $R^3$, $R^4$ and $R^5$ are hydrogen or methyl.

The process can be effected by reacting the appropriate alken-2-ylidene diacylate, e.g. of the formula

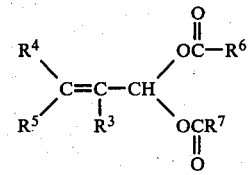

with the aromatic compound in the presence of trifluoroacetic acid (TFA) or by reacting the appropriate α-ethylenic aldehyde with the aromatic compound in the presence of a suitable acid anhydride (e.g. acetic anhydride, propionic anhydride, butyric anhydride etc.) or diketene and trifluoroacetic acid. While it is not intended to be bound to any theory, it is believed that the latter procedure involves either the formation of an alken-2-ylidene diacylate (in situ), or involves the trapping of an intermediate, probably an enol intermediate, formed between the aldehyde and the aryl compound.

The latter procedure, wherein the α-ethylenic aldehyde is added to a mixture of TFA and an anhydride or diketene, is preferred. Any anhydride such as acetic anhydride, propionic anhydride, butyric anhydride and the like would be suitable with the economical acetic anhydride being favored. It is especially preferred, however, to use the mixed anhydride

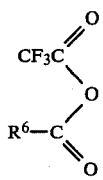

wherein $R^6$ represents an alkanoyl such as acetyl, propionyl, butyryl and the like. Use of the mixed anhydride minimizes the amount of alkanoic acid in the recovered trifluoroacetic acid. While not intending to be bound by any theory, it is surmised that either the diketene reacts with the TFA to form a mixed anhydride (in situ), in which $R^6$ could be

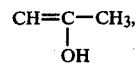

or the diketene could trap an intermediate formed between the aldehyde and the aryl compound, probably an enol intermediate.

The mixed anhydrides can be prepared by methods similar to those known in the art. For example, an alkali metal salt of TFA can be reacted with an alkanoyl halide, e.g. acetyl chloride, propionyl chloride, butyryl chloride etc.); trifluoroacetic anhydride can be reacted with an alkanoic acid; or an alkanoic anhydride can be reacted with trifluoroacetic acid.

In order to minimize the amount of alkanoic acid in the recovered TFA it is preferred to use a method which does not produce the alkanoic acid, e.g. the method using the alkali metal salt of TFA and an alkanoyl halide. In this method the salt of TFA is conveniently prepared in situ by mixing TFA in a solvent, e.g. the aromatic reactant, and neutralising the acid with a concentrated aqueous alkali metal hydroxide. There follows a azeotropic drying period, this being the shorter the more concentrated the hydroxide solution used to prepare the TFA salt. To the suspension of the TFA salt in the solvent, there is now added the alkanoyl halide, preferably the chloride. This addition is suitably done at room temperature, although slightly elevated temperatures do not interfere, e.g. temperatures up to 50° C.

Alternatively, the mixed anhydride can be obtained by mixing the trifluoroacetic acid anhydride with an equimolar amount of an alkanoic acid in a solvent, e.g. the aromatic reactant. One could also add an alkanoic anhydride to trifluoroacetic acid. In this case, alkanoic acid is formed as a by-product.

Alternatively the mixed anhydride may be replaced entirely by using an equimolar quantity of diketene. While not intending to be bound to any particular theory, it is probable that the diketene reacts with the TFA to form the mixed anhydride in situ.

The schematic for the preferred process as applied to prepare the preferred odorants of formula I can be represented as follows:

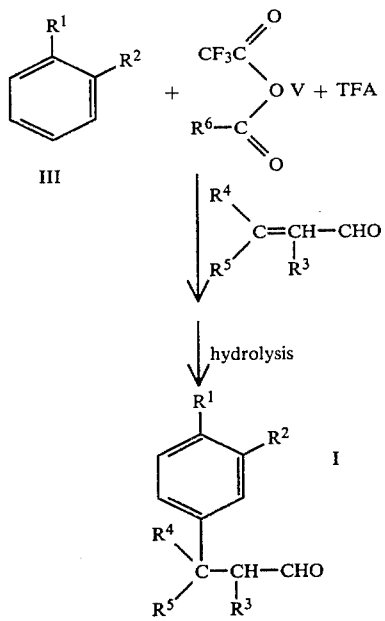

wherein: R¹ through R⁶ are as defined previously.

In the preferred process of this invention it is preferred to add the α-ethylenic aldehyde (e.g. II) to a mixture of the aromatic compound (e.g. III), the mixed anhydride or diketene and the TFA. Molar ratios are not critical to the formation of product but it is preferred to use one mole of the mixed anhydride or diketene per mole of α-ethylenic aldehyde to be used.

Since most of the unreacted aromatic compound (e.g. III) can be recovered, it is preferred to use the aromatic compound in excess of the aldehyde (e.g. II). A ratio of aromatic compound to aldehyde (e.g. III/II) of from 5:1 to 1:1 is preferred.

It is preferred to use an excess of TFA, the preferred molar ratio of TFA to aldehyde being from about 3:1 to 12:1.

The reaction temperature does not appear to be critical and the reaction can be run conveniently at room temperature with a temperature of 20° C. to 50° C. being especially preferred.

After the addition of aldehyde is complete, the mixture is allowed to react for a period, about 3-6 hours in most cases. Upon completion of the reaction time it is preferred to remove the volatiles by distillation, the volatiles being primarily TFA and unreacted aromatic compound (e.g. III). While not intending to be bound to any theory, the residue left behind is believed to be a primary reaction product of the structure

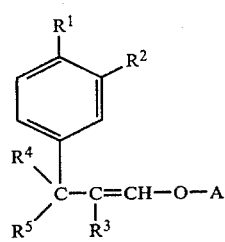

wherein R¹ through R⁵ are as defined previously and A represents an alkanoyl radical when an anhydride or mixed anhydride is used (e.g. CH₃—CO, C₂H₅CO etc.) or the radical

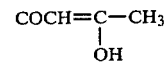

when diketene is used.

The hydrolysis of the primary reaction product, believed to be the compound of formula IV, to give the compound of formula I can be carried out in a manner known per se, see for Example J. Scriabine, Bull, Soc. Chim. France (1961), 1194–1198. The hydrolysis can thus be effected under acid or alkaline conditions. The hydrolysis is for example suitably effected in the presence of a solvent, e.g. an alcoholic solvent. Convenient systems are methanol/water/NaOH or K₂CO₃, or isopropanol/water/H₂SO₄.

EXAMPLE 1

Into a 500 ml 4 necked flask fitted with a mechanical stirrer, thermometer, Dean and Stark reflux head and dropping funnel, there are charged 90 g (0.75 m) cumene, 35 g (1.9 m) water, 35.7 g (0.313 m) trifluoroacetic acid. With stirring there are added 12.5 g (0.313 m) sodium hydroxide dissolved in 15 ml water.

When the addition is complete the mixture is heated to reflux and the water is collected as it azeotropes off. The pot temperature increases from 100° C. to 155° C.

when all the water has been removed. This results in a suspension of the T.F.A. salt in cumene. The total water recovery is 55.6 ml.

The mix is cooled to 20° C. and 220 g (1.92 m) T.F.A. is added, followed by 24.6 g (0.313 m) acetyl chloride. There is only a slight temperature rise of a few degrees. The mixture is stirred at 20°–25° C. for 1 hour in which time the mixed anhydride is formed and sodium chloride precipitates out as a fine suspension. 21.9 g (0.313 m) Methacrolein is then added over a 30 minute period so that the temperature does not rise above 30° C. (A water bath is used for cooling). The mixture is then stirred at 20°–25° C. for a further 6 hour period. The apparatus is then set up for vacuum distillation with a short, packed, fractionating column, a Liebig condenser, a fraction take off unit and vacuum cold trap cooled with liquid nitrogen. The flask is heated in an oil bath while being stirred with a magnetic stirrer. The distillate is recovered under vacuum (0.2 mm Hg) to a maximum pot temperature of 110° C. When all the T.F.A. has been removed the enolic mono acetate (EMA) crude becomes lighter in colour. The crude monoacetate is cooled and the vacuum released.

| | |
|---|---|
| Wt. of Distillate = | 292 g (containing mainly (T.F.A.)) |
| Wt. of crude monoacetate = | 87 g |

The distillate may be recycled for the next experiment then a smaller quantity of cumene is required, i.e. 38 g.

HYDROLYSIS OF THE MONOACETATE TO CYCLAMEN ALDEHYDE 80 ml Methanol are made alkaline to a pH 9–10 and are then added to the crude E.M.A. A solution of 8 g sodium hydroxide in 10 ml water is added with stirring to the mixture so that the temperature does not rise above 40° C. When addition is complete, the mixture is heated and the methanol distilled off to a maximum pot temperature of 100° C. The methanol can be recycled. The mixture is cooled and washed with 2×75 ml water and then vacuum distilled to a maximum temperature of 150° C. (0.1 mm Hg). There are obtained 42.3 g of distillate containing 36 g Cyclamen Aldehyde plus some unknown high boiling impurities (by G.L.C.). Weight of the residue in the flask 75 g.

The purity of the Cyclamen Aldehyde is 98%.

EXAMPLE 2

50 g (0.416 m) Cumene, 21.3 g (0.208 m) acetic anhydride and 150 g (1.27 m) T.F.A. are mixed and 14.5 g (0.207 m) methacrolein is added over 15 mins., maintaining the temperature at 20°–26° C. The mixture is stirred for 6 hours at 20° C. and then distilled under vacuum to a maximum pot temperature of 110° C. The weight of the distillate is 193.5 g (assumed to be T.F.A.+acetic acid+cumene). The residue (20 g) is refluxed for 3 hours with 34 g methanol, 17.5 g potassium carbonate and 33 g water. G.L.C. indicates that hydrolysis is complete. The methanol is distilled off and the mixture extracted with 50 ml diethyl ether and washed with 2×50 ml water. The organic layer is then distilled under vacuum to give 23 g Cyclamen Aldehyde. (10% o- and 90% p-isomers) (53.9% theory). The residue weighs 6.0 g.

EXAMPLE 3

124 g (1.04 m) Cumene, 34.8 g (0.41 m) diketene and 264 g. T.F.A. are mixed and 29 g. (0.41 m) methacrolein is added over 15 minutes maintaining the temperature at 20°–26° C. The mixture is stirred at 20° C. as in Example 1 and then distilled under vacuum to a maximum pot temperature of 110° C. The weight of distillate is 383 g. (T.F.A.+cumene). The residue (68.8 g) is hydrolysed as in Example 1 to give 24.7 g Cyclamen Aldehyde.

EXAMPLE 4

Using the conditions of Examples 1, 2 or 3, the following products were obtained in yields comparable to those achieved in Examples 1 and 2:

(α) 3-[p.tert. butylphenyl]-2-methyl-propionaldehyde from tertiary butylbenzene and methacrolein.

(β) 3-[p-methoxyphenyl]-2-propionaldehyde from methoxybenzene and methacrolein.

(γ) 3-[p-tert. butylphenyl]-propionaldehyde from tertiary butylbenzene and acrolein.

(δ) 3-[p-tert. butylphenyl]-3-methyl-propionaldehyde from tertiary butylbenzene and crotonaldehyde.

We claim:

1. A process for the manufacture of a 3-aryl propionaldehyde which comprises reacting an alken-2-ylidene diacylate or an α-ethylenic aldehyde with an aromatic compound in the presence of trifluoroacetic acid.

2. The process of claim 1 wherein an aromatic compound is reacted with
   (i) an alken-2-ylidene diacylate, or with
   (ii) an α-ethylenic aldehyde and an acid anhydride or diketene in the presence of trifluoroacetic acid and hydrolyzing the intermediate formed.

3. The process of claim 1 wherein an α-ethylenic aldehyde is added to a mixture of trifluoroacetic acid, the aromatic compound, and an acid anhydride or diketene.

4. A process according to claims 1 or 2 wherein an alken-2-ylidene diacylate of the formula

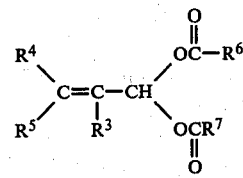

is reacted with an aromatic compound of the formula

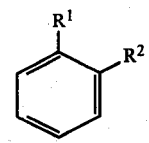

III to provide a 3-arylpropionaldehyde of the formula

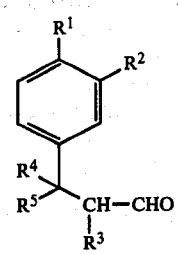

I wherein:

R¹ is isopropyl, n-butyl, sec-butyl, iso-butyl, t-butyl or methoxy when R² is hydrogen; or R¹ together with R² represents the methylenedioxy group;

R³, R⁴ and R⁵ are hydrogen or methyl;

R⁶ is methyl, ethyl, propyl, butyl or

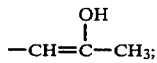

and

R⁷ is methyl, ethyl, propyl, butyl or trifluoromethyl.

5. A process according to claims 1 or 2 wherein an α-ethylenic aldehyde of the formula

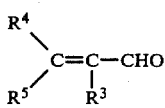   II is added to a mixture of the aromatic compound

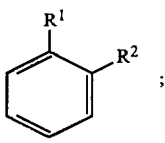   III the acid anhydride

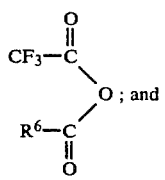   V and trifluoroacetic acid to provide a 3-arylpropionaldehyde of the formula

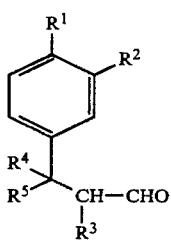   I wherein:
R¹ is isopropyl, n-butyl, sec-butyl, iso-butyl, t-butyl or methoxy when R² is hydrogen; or
R¹ together with R² represents the methylenedioxy group;
R³, R⁴ and R⁵ are hydrogen or methyl; and
R⁶ is methyl, ethyl, propyl, butyl or

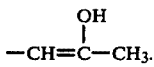

6. A process according to claim 1 wherein there is used (i) between 3 moles and 12 moles of trifluoroacetic acid; and (ii) between 1 mole and 5 moles of aromatic compound for each mole of alken-2-ylidene diacylate or α-ethylenic aldehyde to be reacted and wherein there is used one mole of acid anhydride for each mole of α-ethylenic aldehyde.

7. A process according to claim 6 wherein one equivalent of an α-ethylenic aldehyde of the formula

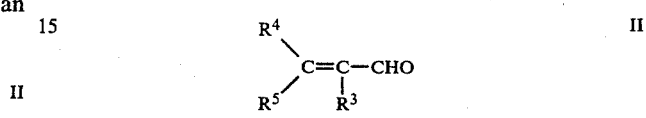   II is added to a mixture comprising (i) one to three equivalents of the aromatic compound

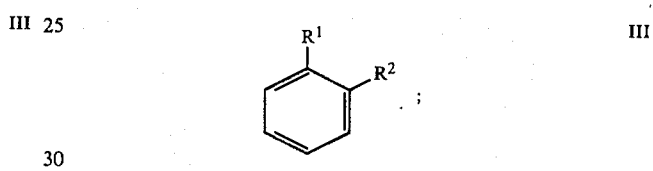   III (ii) one equivalent of the mixed anhydride

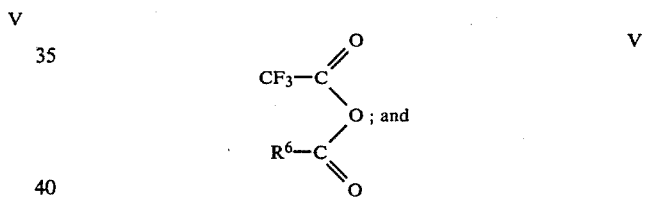   V and (iii) three to twelve equivalents of trifluoroacetic acid wherein:
R¹ is isopropyl, n-butyl, sec-butyl, isobutyl, t-butyl or methoxy when R² is hydrogen; or
R¹ together with R² represents the methylenedioxy group;
R³, R⁴ and R⁵ are hydrogen or methyl; and
R⁶ is methyl, ethyl, propyl, butyl or

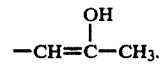

8. A process according to claims 1, 2 or 7 wherein the excess trifluoroacetic acid and aryl compound is separated from the primary reaction product and the primary reaction product is hydrolyzed to the corresponding 3-arylpropionaldehyde.

9. A process according to claims 1, 2 or 7 wherein the reaction temperature is from 20° C. to 50° C.

10. A process according to claims 1, 2 or 7 wherein one of the reactants is the mixed anhydride

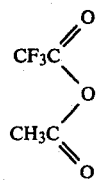 V'

11. The process according to claim 1 wherein one equivalent of an α-ethylenic aldehyde of the formula

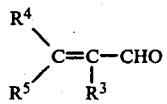 II is added to a mixture comprising (i) one to three equivalents of an aromatic compound of the formula

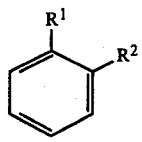 III (ii) one equivalent of the mixed anhydride

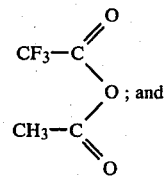 V'

(iii) three to twelve equivalents of trifluoroacetic acid and then, after allowing said mixture to react at 20° C. to 50° C., distilling the volatile components away from the primary reaction product and hydrolyzing said primary reaction product to the desired compound of the formula

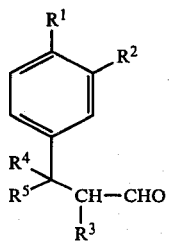 I and isolating said compound,
wherein:
$R^1$ is isopropyl, n-butyl, sec-butyl, iso-butyl, t-butyl or methoxy when $R^2$ is hydrogen; or
$R^1$ together with $R^2$ represents the methylenedioxy group; and
$R^3$, $R^4$ and $R^5$ are hydrogen or methyl.

12. Process according to claims 1,2,7 or 11 where methacrolein is reacted with isopropylbenzene.

13. Process according to claims 1,2,7 or 11 wherein methacrolein is reacted with tert. butylbenzene.

14. Process according to claims 1,2,7 or 11 wherein methacrolein is reacted with methylenedioxy benzene.

15. Process according to claims 1,2,7 or 11 wherein methacrolein is reacted with anisol.

16. Process according to claims 1,2,7 or 11 wherein acrolein is reacted with isopropyl benzene, t-butyl benzene, methylenedioxy benzene or anisole.

* * * * *